United States Patent
Omidi

(10) Patent No.: US 8,789,542 B2
(45) Date of Patent: Jul. 29, 2014

(54) MULTI-EDGE DENTAL FLOSS

(76) Inventor: Julian Omidi, Las Vegas, NV (US)

(*) Notice: Subject to any disclaimer, the term of this patent is extended or adjusted under 35 U.S.C. 154(b) by 44 days.

(21) Appl. No.: 13/341,920

(22) Filed: Dec. 31, 2011

(65) Prior Publication Data

US 2012/0167911 A1 Jul. 5, 2012

Related U.S. Application Data

(60) Provisional application No. 61/428,986, filed on Dec. 31, 2010.

(51) Int. Cl.
*A61C 15/00* (2006.01)
*A61C 15/04* (2006.01)
*A61C 15/02* (2006.01)

(52) U.S. Cl.
CPC .......... *A61C 15/041* (2013.01); *A61C 15/046* (2013.01); *A61C 15/02* (2013.01); *A61C 15/043* (2013.01)
USPC ............................ 132/321; 132/329; 132/325

(58) Field of Classification Search
CPC ........ A61C 15/00; A61C 15/02; A61C 15/04; A61C 15/041; A61C 15/042; A61C 15/046; A61C 15/047; A45C 11/008
USPC ................ 132/321, 200, 286, 309, 322–329; 206/581, 823, 368, 63.5; 118/14, 39, 118/40, 36, 420; 427/175, 385.5, 2.29; 250/455.11; 225/6; 264/16; 222/129; 242/169–171, 525.6, 526.1, 526.2
See application file for complete search history.

(56) References Cited

U.S. PATENT DOCUMENTS

| | | | | |
|---|---|---|---|---|
| 3,830,247 A * | 8/1974 | Kaphalakos | .................. | 132/322 |
| 3,847,167 A * | 11/1974 | Brien | ............................. | 132/322 |
| 4,019,522 A * | 4/1977 | Elbreder | ...................... | 132/322 |
| 4,162,688 A * | 7/1979 | Tarrson et al. | ................ | 132/322 |
| 4,245,658 A * | 1/1981 | Lecouturier | .................. | 132/322 |
| 4,646,766 A * | 3/1987 | Stallard | ........................ | 132/325 |
| 4,806,770 A * | 2/1989 | Hylton et al. | ............ | 250/455.11 |
| 4,888,487 A * | 12/1989 | Ritter | ....................... | 250/455.11 |
| 4,973,847 A * | 11/1990 | Lackey et al. | ............ | 250/455.11 |
| 5,029,252 A * | 7/1991 | Ameseder | ................ | 250/455.11 |
| 5,063,948 A * | 11/1991 | Lloyd | ........................... | 132/321 |
| 5,065,861 A * | 11/1991 | Greene et al. | ................ | 206/63.5 |
| 5,176,157 A * | 1/1993 | Mazza | ......................... | 132/322 |
| 5,199,622 A * | 4/1993 | Vieau | ............................. | 225/51 |
| 5,400,839 A * | 3/1995 | Cravett | ...................... | 141/362 |
| 5,645,206 A * | 7/1997 | Ippisch | .......................... | 225/10 |
| 5,765,739 A * | 6/1998 | Yates, III | ....................... | 225/23 |
| 5,857,471 A * | 1/1999 | Harada | ......................... | 132/321 |
| 5,873,495 A * | 2/1999 | Saint-Germain | ............ | 222/135 |
| 5,896,868 A * | 4/1999 | Kyte | ............................ | 132/322 |
| 6,250,313 B1 * | 6/2001 | Rees | ............................. | 132/321 |
| 6,293,287 B1 * | 9/2001 | Anglin et al. | ................. | 132/321 |
| 6,295,996 B1 * | 10/2001 | Dickie | ........................ | 132/321 |
| 6,398,093 B1 * | 6/2002 | Dolan | ............................ | 225/51 |

(Continued)

*Primary Examiner* — Vanitha Elgart
(74) *Attorney, Agent, or Firm* — David R Preston & Associates; James Fleming

(57) ABSTRACT

The present invention is comprised of an antibacterial dental floss device to provide the user with enhanced dental hygiene care. The present invention is further comprised of processors and modules to fray dental floss to provide more thorough cleaning with bristled floss coated with oral antibacterial compounds to increase prevention of dental and oral infections and disease. The present invention provides an ultraviolet light to further treat dental and oral bacterial presence. The present invention provides the user with a compact portable dental hygiene device.

17 Claims, 6 Drawing Sheets

(56) References Cited

U.S. PATENT DOCUMENTS

| | | | |
|---|---|---|---|
| 6,461,568 B1* | 10/2002 | Eckhardt | 422/24 |
| 6,607,000 B2* | 8/2003 | Marwah et al. | 132/321 |
| 6,705,328 B1* | 3/2004 | Ramirez | 132/322 |
| 7,987,861 B2* | 8/2011 | Grosse | 132/325 |
| 8,256,439 B1* | 9/2012 | Stinson | 132/324 |
| 2004/0155201 A1* | 8/2004 | Russell et al. | 250/455.11 |
| 2007/0012333 A1* | 1/2007 | D'Aquila | 132/325 |
| 2008/0251098 A1* | 10/2008 | Chen | 132/329 |
| 2008/0257377 A1* | 10/2008 | Burrows | 132/322 |
| 2010/0006119 A1* | 1/2010 | Veras et al. | 132/325 |
| 2010/0024722 A1* | 2/2010 | Ochs et al. | 118/244 |
| 2012/0160951 A1* | 6/2012 | Kalbfeld et al. | 242/563.2 |
| 2012/0164343 A1* | 6/2012 | Lee | 427/457 |
| 2012/0167912 A1* | 7/2012 | Booker | 132/322 |

* cited by examiner

MULTI-EDGE DENTAL FLOSS

BACKGROUND

Dental hygiene has long been seen as an area requisite to a healthy life. More recently the growing recognition of its broader importance to overall health has produced a wider array of dental prevention and treatment practices. Dental flossing is one beneficial habit people can take advantage of easily. But current flossing techniques concentrate on food particle removal from the teeth. Other preventive treatments tend to be left in the dentist's office.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of an antibacterial dental floss device is described for illustrative purposes and the underlying method can apply to any number and multiple types of antibacterial dental floss devices. In one embodiment of the present invention, the antibacterial dental floss device is configured to coat the floss with an oral antibacterial compound. In another embodiment the antibacterial dental floss device is configured to provide ultraviolet violet light as an antibacterial treatment powered by batteries and antibacterial dental floss devices can be configured using other forms of treatment coatings and types of light source treatments to provide multiple types of treatment for oral fungal infections, plaque removal and gingivitis and fabricated using various plastics and components or created in other forms, colors, shapes, sizes and depictions using the present invention.

Figure 1:
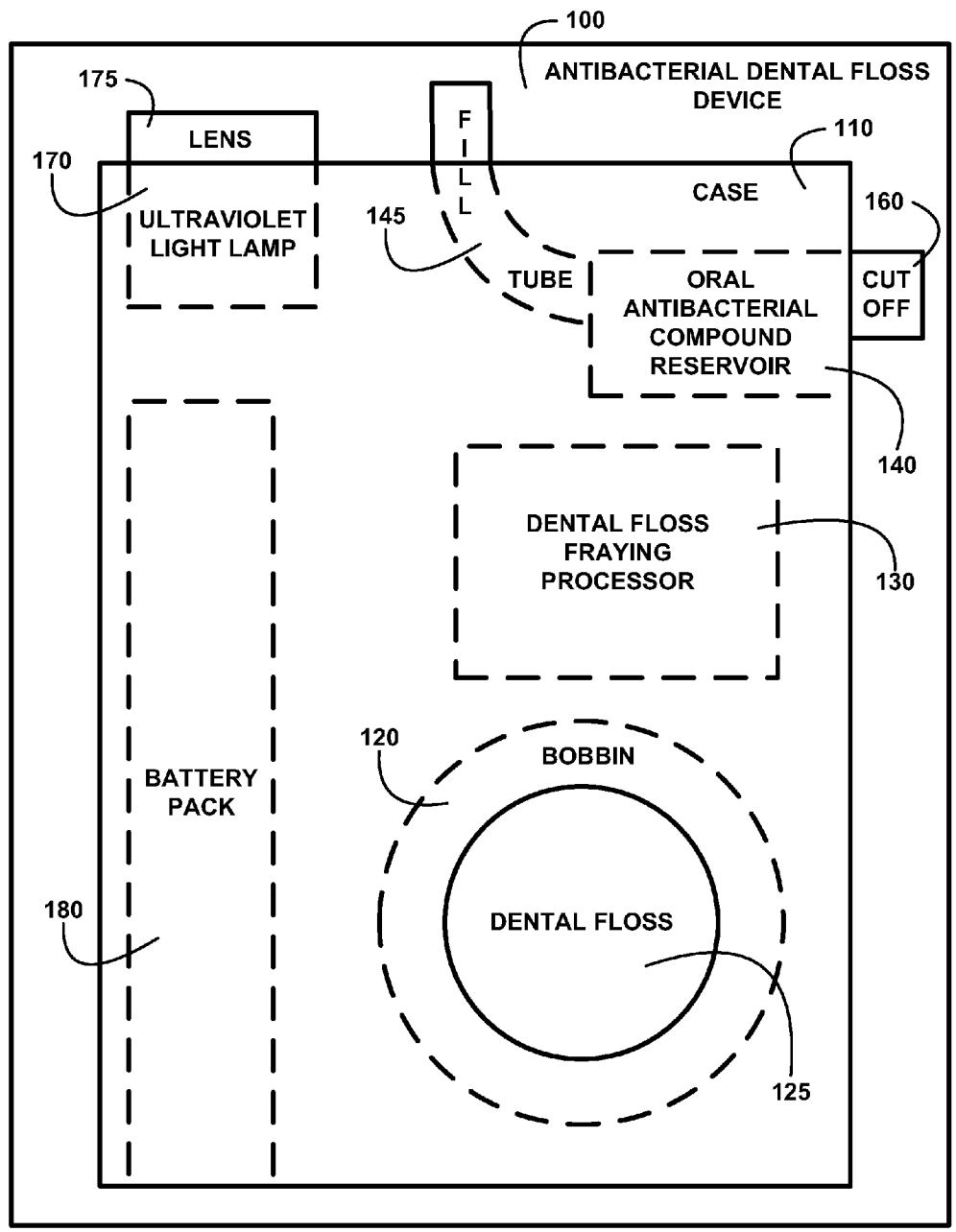
FIG. 1 shows a block diagram of an overview of an antibacterial dental floss device of one embodiment of the present invention.

FIG. 1 shows a block diagram of an overview of an antibacterial dental floss device of one embodiment of the present invention. FIG. 1 shows an antibacterial dental floss device 100 that can be assembled in a compact case 110. The antibacterial dental floss device 100 can be configured with a bobbin 120 which is used to hold a length of a dental floss 125. When a user pulls out a short length of the dental floss 125 from the bobbin 120 it passes over a series of curved guide pins 132 and pulleys 134. The dental floss 125 is routed through a dental floss fraying processor 130 which cuts and frays short sections of a portion of the fibers from which the dental floss 125 is manufactured of one embodiment of the present invention.

The dental floss fraying processor 130 uses electrical power supplied from a battery pack 180 to heat thermal devices to fuse the fibers being cut at a short distance on both sides of the point where the cut is made. Dental floss threads are manufactured in various thicknesses from materials such as polyester, nylon, PTFE and Polymer. These materials can be heated to allow thermal bonding of the fibers to one another. This prevents the cut fibers from being pulled from the floss thread while flossing. The dental floss fraying processor 130 then brushes the cut fibers to create bristles of one embodiment of the present invention.

The bristled dental floss 125 is passed through a oral antibacterial compound reservoir 140 and coated with an oral antibacterial compound, for example antibacterial tooth paste, an all natural ingredient oral antibacterial compound, plaque inhibiting antibacterial compound and antibacterial compounds that contain vitamins. The oral antibacterial compound reservoir 140 can be filled or refilled using a fill tube 145. The user can use a cut off 160 to cut the desired length of bristled dental floss coated with an oral antibacterial compound pulled from the antibacterial dental floss device 100. The user can then apply the antibacterial compound to the teeth and gums while using the bristled floss to remove food particles and brush the tooth surfaces between the narrow spaces that would be difficult to reach with a toothbrush. This will facilitate the removal of plaque and other build up of one embodiment of the present invention.

Once completed with flossing the user can switch on an ultraviolet light lamp 170 built into the antibacterial dental floss device 100 and powered by a battery pack 180. The user will direct the ultraviolet light radiating through the exterior lens 175 of the antibacterial dental floss device 100 to areas inside the mouth including the gums and palate. The germicidal benefits of ultraviolet light will further reduce oral infections. Gum disease can result from bacterial plaque building up between teeth, under the gum line and around dental appliances. The antibacterial dental floss device 100 provides enhanced bristled flossing to better clean the space between teeth, applies an antibacterial compound to the area between teeth, under the gum line and around dental appliances combined with ultraviolet light as an additional germicidal treatment. The antibacterial dental floss device 100 helps fight gum diseases, helps reduce plaque buildup and provides the user with access to advanced oral hygiene treatments in a compact portable device of one embodiment of the present invention.

Detailed Operation:

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

Figure 2:
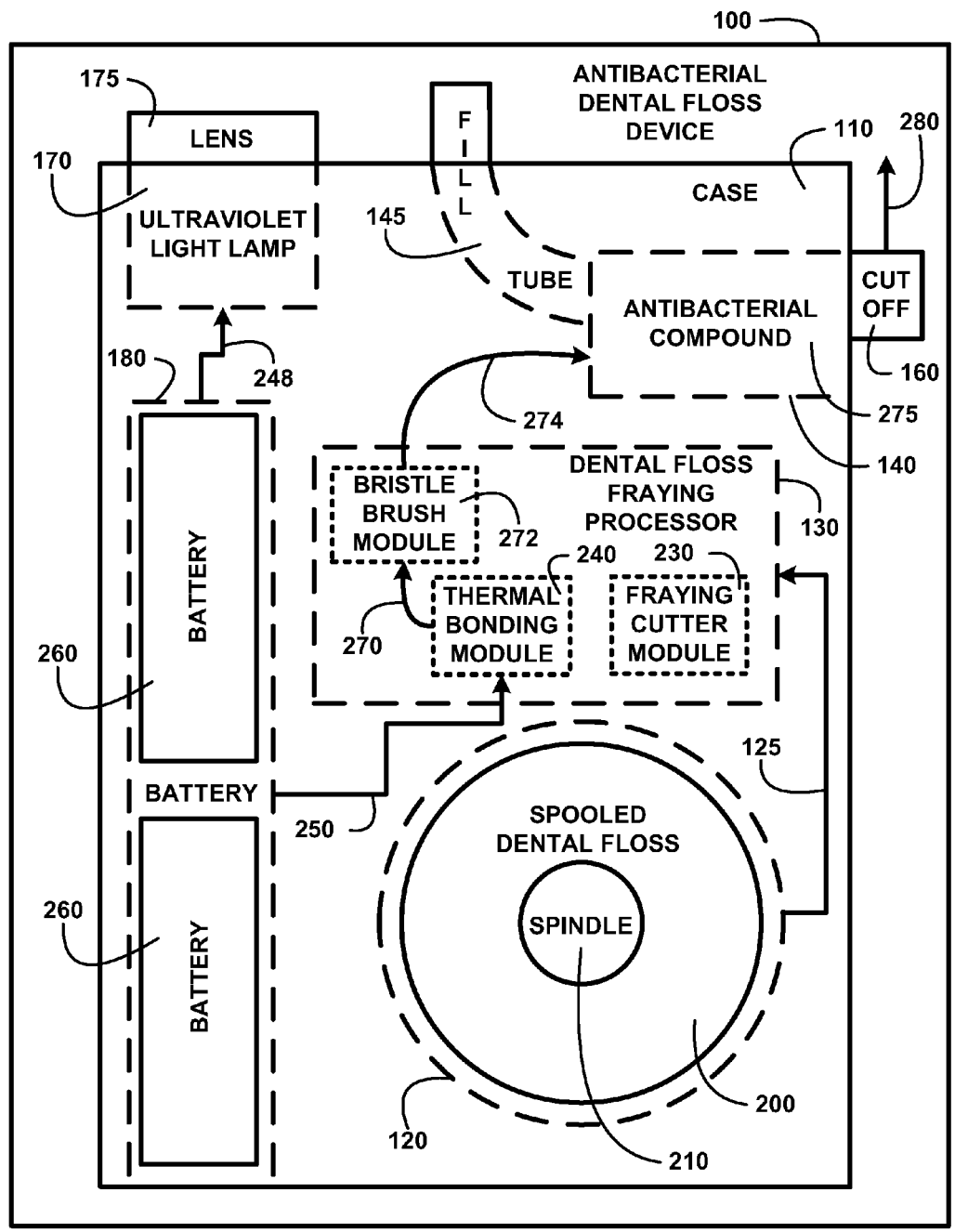
FIG. 2 shows a block diagram of an overview flow chart of an antibacterial dental floss device of one embodiment of the present invention.

FIG. 2 shows a block diagram of an overview flow chart of an antibacterial dental floss device of one embodiment of the present invention. FIG. 2 shows the antibacterial dental floss device 100 in the case 110 that can be manufactured from materials for example plastic. The bobbin 120 is installed on a spindle 210 to allow spooled dental floss 200 to play off the bobbin 120 when pulled by the user. The unwinding dental floss 125 enters the dental floss fraying processor 130. The dental floss fraying processor 130 can be configured with one or more fraying cutter module 230 to cut the outer layers of fibers of the floss thread. The cutting blades 136 of the fraying cutter module 230 can be configured to be attached in the inner curved area of a pulley channel 138 as a crescent shaped blade to allow radial cuts of one embodiment of the present invention.

The dental floss fraying processor 130 can be configured with one or more thermal bonding module 240 to fuse fibers a short distance on both sides of the cut. The thermal bonding module 240 is heated by a thermal bonding electrical circuit 250 passing through the thermal bonding module 240 components that are sized to produce resistance to the electrical current and heat sufficiently to fuse the fiber material. The heated-elements 139 of the thermal bonding module can be configured to be attached in the inner curved area of a pulley channel 138 in a crescent shape to allow radial fusing. The thermal bonding electrical circuit 250 draws electricity from one or more battery 260 installed in the battery pack 180 of one embodiment of the present invention.

The fused cuts produce a frayed dental floss 270 that is routed through a bristle brush module 272. The bristle brush module 272 combs the cut fibers away for the main floss thread to produce a bristled dental floss 274. The bristled dental floss 274 enters the oral antibacterial compound reservoir 140 and bathes the bristled dental floss 274 in an antibacterial compound 275 of one embodiment of the present invention. The antibacterial compound 275 is placed in the oral antibacterial compound reservoir 140 using the fill tube 145. The antibacterial compound 275 can be configured for example as a liquid, gel or paste and can be an over the counter product or prescription medication. The bristled dental floss 274 becomes coated or soaked in the antibacterial compound 275 before being separated using the cut off 160. The antibacterial coated bristled dental floss 280 is now available for the user to floss their teeth using the bristled dental floss 274 to brush in between teeth and reach the area of the teeth and gums not accessible with a tooth brush. This allows the user to remove plaque and other build up not just food particles while flossing. The antibacterial compound 275 will be applied to those same hard to reach areas where bacteria and other materials or organisms generally start gum diseases and plaque buildup of one embodiment of the present invention.

The user can treat the oral cavity in its entirety using the ultraviolet light lamp 170 built into the antibacterial dental floss device 100. The user can push a switch button to open an ultraviolet light switched electrical circuit 248 to conduct electricity from one or more battery 260 in the battery pack 180. The electricity through the ultraviolet light switched electrical circuit 248 will power up the ultraviolet light lamp 170. The ultraviolet light lamp 170 will radiate ultraviolet light through the lens 175 into the oral cavity as directed by the user. The benefits of the germicidal ultraviolet light illumination will aid in combating bacteria and other organisms in areas not normally contacted in brushing or flossing for example the roof of the mouth, rear inner cheek tissues and under the tongue. The antibacterial dental floss device 100 can be configured to include an AC current adapter plug-in to allow rechargeable batteries to be installed in the battery pack 180 of one embodiment of the present invention.

The ability of the antibacterial dental floss device 100 to fill prescribed medication into the oral antibacterial compound reservoir 140 provides dentist and other oral specialist the opportunity to effectively treat patients in an outpatient mode. The outpatient can effectively administer those prescribed medications using the same familiar techniques of flossing and save expensive treatment visits to the dental office. The compact portable antibacterial dental floss device 100 can enable a user to easily enhance their preventative oral hygiene to reduce gum disease and bacterial plaque build-up of one embodiment of the present invention.

Figure 3:
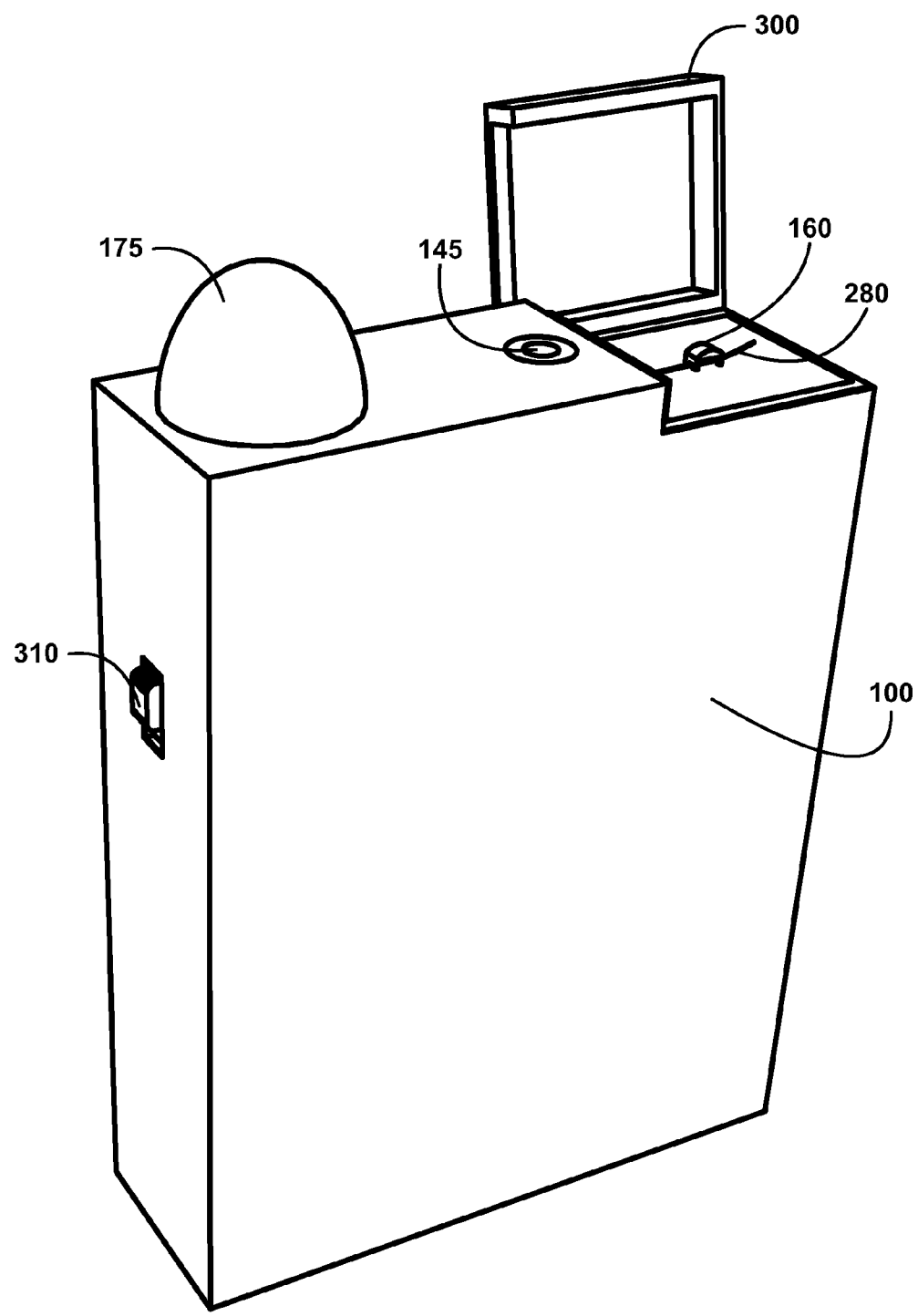
FIG. 3 shows for illustrative purposes only an example of an antibacterial dental floss device in a prospective view of one embodiment of the present invention.

Antibacterial Dental Floss Device:

FIG. 3 shows for illustrative purposes only an example of an antibacterial dental floss device in a prospective view of one embodiment of the present invention. FIG. 3 shows the antibacterial dental floss device 100 which is a compact advanced dental hygiene device. The portable case 110 of FIG. 1 contains the spooled dental floss 200 of FIG. 2, dental floss fraying processor 130 of FIG. 1, oral antibacterial compound reservoir 140 of FIG. 1 and antibacterial compound 275 of FIG. 2 used to supply the user with antibacterial coated bristled dental floss 280. The user can close a case cover 300 to maintain a clean supply after pulling out and cutting the desired length of the antibacterial coated bristled dental floss 280 using the cut off 160. The fill tube 145 can be configured to include a removable plug or a permanent sealed cap after filling of one embodiment of the present invention.

The antibacterial dental floss device 100 can be configured to include a switch 310 for example on the side or top to open the ultraviolet light switched electrical circuit 248 of FIG. 2 to operate the ultraviolet light lamp 170 of FIG. 1 which radiates ultraviolet light through the lens 175. The antibacterial dental floss device 100 illustrated in FIG. 3 shows an unobtrusive compact and portable configuration of one embodiment of the present invention.

Figure 4A:
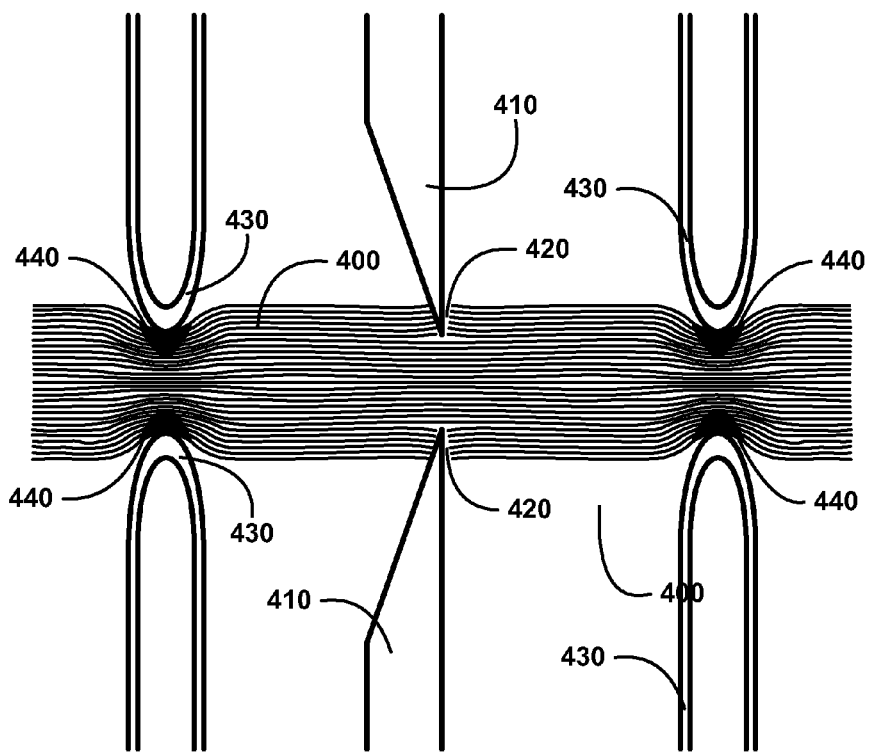
FIGS. 4A and 4B shows for illustrative purposes only an example of an antibacterial dental floss device floss fraying process of one embodiment of the present invention.

Floss Fraying Process:

FIG. 4A shows for illustrative purposes only an example of an antibacterial dental floss device floss fraying process of one embodiment of the present invention. The antibacterial dental floss device 100 of FIG. 1 includes the dental floss fraying processor 130 of FIG. 1 to produce the bristled dental floss 274 of FIG. 2. This process starts with the dental floss 125 of FIG. 1 entering the dental floss fraying processor 130 of FIG. 1 from the bobbin 120 of FIG. 1. The floss thread is made up of dental floss fibers 400. The fraying process uses a thermal bonding module 240 of FIG. 2 configured with a thermal bonder 430 which is the heated element to fuse the dental floss fibers 400 creating a section of bonded fibers 440. The fraying cutter module 230 of FIG. 2 is configured with a fraying cutter 410 to cut fibers 420 between two sections of bonded fibers 440 to produce the frayed dental floss 270 of FIG. 2. The frayed dental floss 270 of FIG. 2 then travels to the bristle brush module 272 of FIG. 2 of one embodiment of the present invention.

Figure 4B:
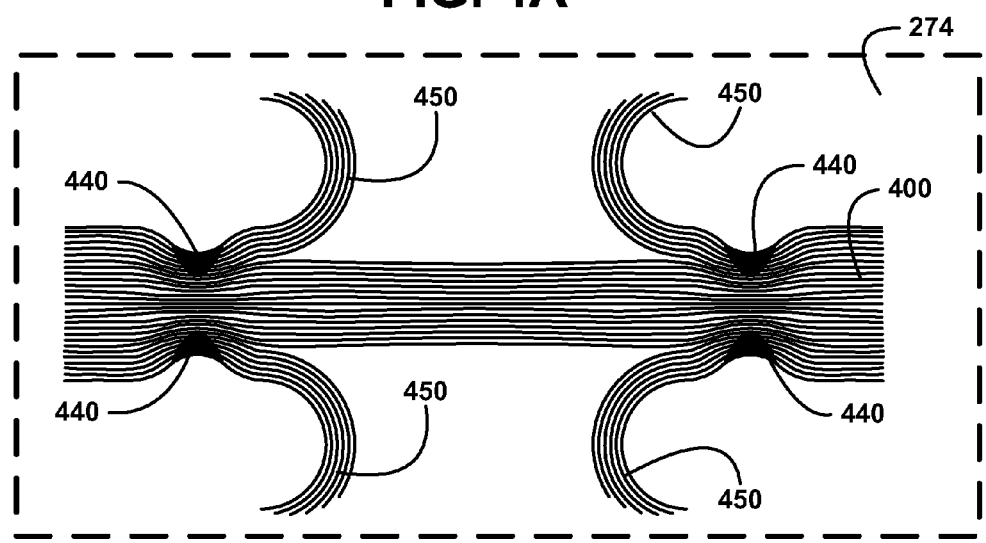

Bristled Dental Floss:

FIG. 4B shows for illustrative purposes only an example of an antibacterial dental floss device bristled dental floss of one embodiment of the present invention. FIG. 4B shows the frayed dental floss 270 of FIG. 2 after it travels through the bristle brush module 272 of FIG. 2. The dental floss fraying processor 130 of FIG. 1 uses the bristle brush module 272 of FIG. 2 to further process the frayed dental floss 270 of FIG. 2 made of dental floss fibers 400. The cut fibers 420 of FIG. 4A between the two sections of bonded fibers 440 are brushed back against the section of bonded fibers 440 to which they are still connected. The bristle brush module 272 of FIG. 2 is configured for example to exert sufficient force to bend the cut fibers 420 of FIG. 4A. The bent cut fibers 420 of FIG. 4A form brushed cut fibers 450 to maintain an outward pointing position to form a bristle. The brushed cut fibers 450 positioned along the floss thread create the bristled dental floss 274 of FIG. 2 of one embodiment of the present invention.

Figure 5:
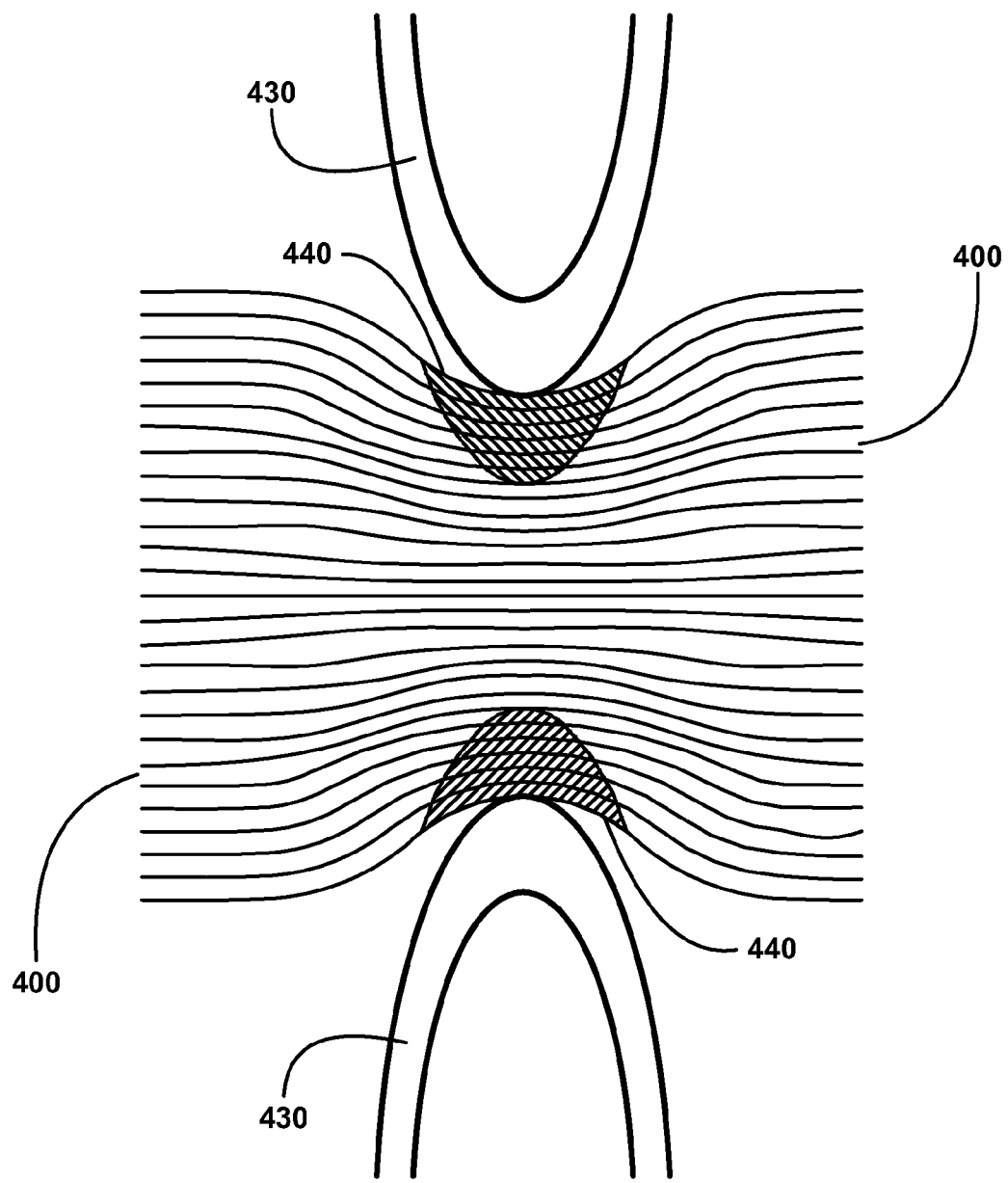
FIG. 5 shows for illustrative purposes only an example of an antibacterial dental floss device floss fiber thermal bonding process of one embodiment of the present invention.
Figure 6:
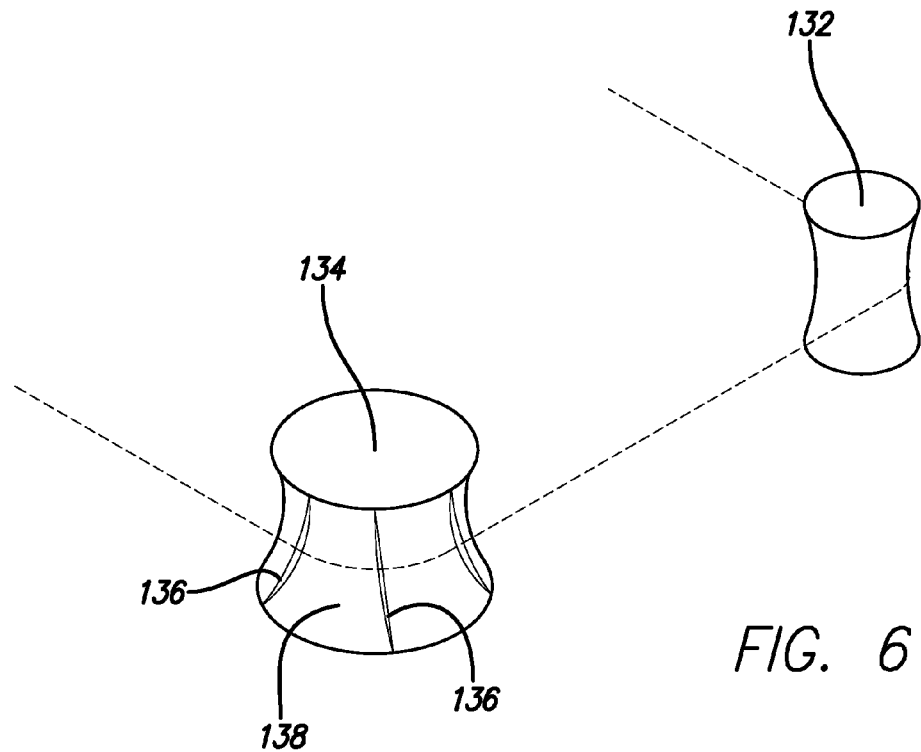
FIG. 6 shows for illustrative purposes only an example of a curved guide pin and pulley with crescent shaped blades within the pulley channel.
Figure 7:
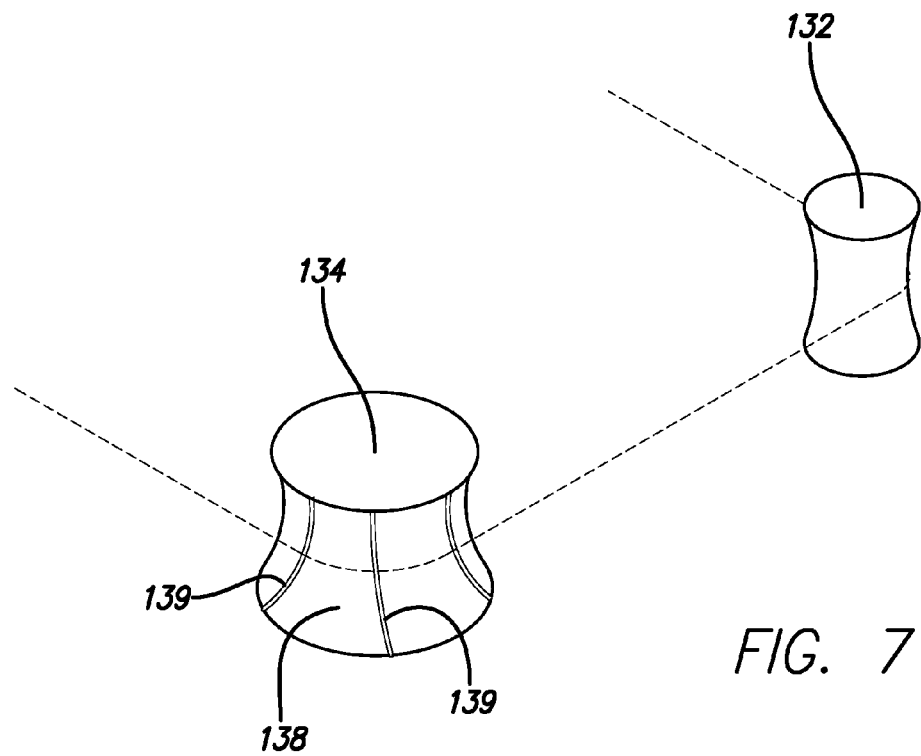
FIG. 7 shows for illustrative purposes only an example of a curved guide pin and pulley with crescent shaped resistance heating elements within the pulley channel.

Thermal Bonding Process:

FIG. 5 shows for illustrative purposes only an example of an antibacterial dental floss device floss fiber thermal bonding process of one embodiment of the present invention. FIG. 5 shows a section of the dental floss fibers 400. The dental floss fibers 400 of the dental floss 125 of FIG. 1 are traveling through the thermal bonding module 240 of FIG. 2 of the dental floss fraying processor 130 of FIG. 1. The thermal bonder 430 of the thermal bonding module 240 of FIG. 2 has been heated by the resistance to the battery 260 of FIG. 2 current flow in the thermal bonding electrical circuit 250 of FIG. 2. The dental floss fibers 400 in contact with the thermal bonder 430 and those dental floss fibers 400 in close proximity are heated sufficiently to cause the fiber materials to soften and fuse to one another to form bonded fibers 440. The thermal bonder 430 can be configured of conductive materials for example stainless steel, aluminum or copper coated with a non-stick material such as Teflon to prevent the dental floss fibers 400 from adhering during the fusing process. The thermal bonder 430 conductive materials can be configured of a size and shape to create an electrically resistive capacity to produce the desired heating temperature to cause the desired fusing of the dental floss fibers 400 materials of one embodiment of the present invention.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A dental floss dispenser comprising:
   a case,
   a bobbin disposed within the case, wherein the bobbin has a length of dental floss spooled therearound, and wherein the dental floss comprises layers of fibers,
   a dental floss fraying processor disposed in the case, wherein the dental floss fraying processor includes a fraying cutter module configured to cut outer layers of the dental floss fibers thereby providing outer layers of fibers that have been cut and inner layers of fibers that have not been cut, and wherein the dental floss fraying processor includes a power supply and a thermal bonding module configured to thermally fuse some layers of fibers, and
   a cut-off disposed on the case and configured to cut and separate a desired length of dental floss,
   wherein the dental floss is configured to travel in a path from the bobbin, through the dental floss fraying processor, and to the cut-off, such that the desired length of dental floss cut and separated by the cut-off is a bristled dental floss.

2. The dispenser of claim 1 wherein the dental floss fraying processor include a bristle brush module configured to comb the cut fibers away from the inner layers of fibers to produce the bristled dental floss.

3. The dispenser of claim 1 further comprising
   an ultraviolet light disposed in the case,
   a lens associated with the case and configured to direct the light radiated from the ultraviolet light, and
   a power supply for providing power to the dental floss fraying processor and the ultraviolet light.

4. The dispenser of claim 1 further comprising curved guide pins and channel pulleys for directing the dental floss along the path.

5. A dental floss dispenser comprising:
   a case,
   a bobbin disposed within the case, wherein the bobbin has a length of dental floss spooled therearound, and wherein the dental floss comprises layers of fibers,
   curved guide pins and channel pulleys for directing the dental floss along a path,
   a dental floss fraying processor disposed in the case, wherein the dental floss fraying processor includes a fraying cutter module configured to cut outer layers of the dental floss fibers thereby providing outer layers of fibers that have been cut and inner layers of fibers that have not been cut and wherein the fraying cutter module includes cutting blades that are attached within a channel of at least one of said pulleys,
   a cut-off disposed on the case and configured to cut and separate a desired length of dental floss,
   wherein the dental floss is configured to travel in a path from the bobbin, through the dental floss fraying processor, and to the cut-off, such that the desired length of dental floss cut and separated by the cut-off is a bristled dental floss.

6. The dispenser of claim 5 wherein the cutting blades are crescent shaped to provide radial cuts.

7. The dispenser of claim 1 wherein the thermal bonding module includes a thermal bonder that includes resistance heating elements for fusing dental floss fibers to one another.

8. The dispenser of claim 7 wherein the resistance heating elements are attached within a pulley channel.

9. The dispenser of claim 8 wherein the resistance heating elements are formed in a crescent shape to provide radial fusing.

10. The dispenser of claim 1 further comprising an antibacterial compound reservoir disposed in the case, wherein the dental floss is configured to travel in a path from the bobbin, through the dental floss fraying processor, through the antibacterial compound reservoir and to the cut-off, such that the desired length of dental floss cut and separated by the cut-off is a bristled dental floss coated with an antibacterial compound.

11. The dispenser of claim 10 further comprising a fill tube configured to allow filling or injection of an oral antibacterial compound into the antibacterial compound reservoir.

12. A dental floss dispenser comprising:
   a case,
   a bobbin disposed within the case, wherein the bobbin has a length of dental floss spooled therearound, and wherein the dental floss comprises layers of fibers,
   a dental floss fraying processor disposed in the case, wherein the dental floss fraying processor includes a fraying cutter module configured to cut out layers of the dental floss fibers thereby providing outer layers of fibers that have been cut and inner layers of fibers that have not been cut, and wherein the dental floss fraying processor includes a thermal bonding module configured to thermally fuse some layers of fibers
   a cut-off disposed on the case and configured to cut and separate a desired length of dental floss,
   an ultraviolet light disposed in the case, a lens associated with the case and configured to direct light radiated from the ultraviolet light, and a power supply for providing power to the ultraviolet light.

13. The dispenser of claim 12 wherein the power supply comprises a rechargeable battery.

14. The dispenser of claim 12 wherein the dental floss fraying processor includes a bristle brush module configured to comb the cut fibers away from the inner layers of fibers to produce the bristled dental floss.

15. The dispenser of claim 12 further comprising an antibacterial compound reservoir disposed in the case, wherein the dental floss is configured to travel in a path from the bobbin, through the antibacterial compound reservoir and to the cut-off.

16. A dental floss dispenser comprising:

a case, a bobbin disposed within the case, wherein the bobbin has a length of dental floss spooled therearound, and wherein the dental floss comprises layers of fibers, a dental floss fraying processor disposed in the case, wherein the dental floss fraying processor includes a fraying cutter module configured to cut out layers of the dental floss fibers thereby providing outer layers of fibers that have been cut and inner layers of fibers that have not been cut, and wherein the dental floss fraying processor includes a power supply and a thermal bonding module configured to thermally fuse some layers of fibers, and an antibacterial compound reservoir disposed in the case, wherein the dental floss is configured to travel in a path from the bobbin, through the antibacterial compound reservoir and to a cut-off, such that a desired length of dental floss cut and separated by the cut-off is coated with an antibacterial compound.

17. The dispenser of claim 16 further comprising a fill tube configured to allow filling or injection of an antibacterial compound into the antibacterial compound reservoir.

* * * * *